United States Patent [19]

Jones

[11] 4,216,334

[45] Aug. 5, 1980

[54] IMIDAZOLINE SALTS OF ACID PHOSPHONATES

[75] Inventor: Daniel G. Jones, Cherry Hill, N.J.

[73] Assignee: Mobil Oil Corporation, New York, N.Y.

[21] Appl. No.: 8,456

[22] Filed: Feb. 1, 1979

Related U.S. Application Data

[60] Continuation-in-part of Ser. No. 840,924, Oct. 11, 1977, abandoned, which is a division of Ser. No. 733,581, Oct. 18, 1976, Pat. No. 4,070,294, which is a continuation-in-part of Ser. No. 544,245, Jan. 27, 1975, abandoned, which is a continuation-in-part of Ser. No. 386,481, Aug. 7, 1973, abandoned.

[51] Int. Cl.² ........................................... C07D 233/14
[52] U.S. Cl. .................................... 548/352; 548/347; 548/353; 252/32.5
[58] Field of Search .................... 548/347, 353, 352

[56] References Cited

U.S. PATENT DOCUMENTS

| Re. 23,227 | 5/1950 | Blair, Jr. et al. ............... | 548/352 |
|---|---|---|---|
| 3,514,399 | 5/1970 | Robinson ....................... | 548/347 |
| 3,584,008 | 6/1971 | Redmore ........................ | 548/352 |
| 3,585,210 | 6/1971 | Redmore ........................ | 548/352 |
| 3,674,804 | 7/1972 | Redmore ........................ | 548/352 |
| 3,793,199 | 2/1974 | Schlicht ........................ | 252/32.5 |
| 4,052,324 | 10/1977 | Braid ........................... | 548/352 |
| 4,125,472 | 11/1978 | Braid ........................... | 548/347 |

FOREIGN PATENT DOCUMENTS 668735  8/1963  Canada .................................. 548/352

*Primary Examiner*—Natalie Trousof
*Attorney, Agent, or Firm*—Charles A. Huggett; Raymond W. Barclay; Howard M. Flournoy

[57] ABSTRACT

Salts of (a) an alkyl, long chain alkyl acid phosphonate having the formula:

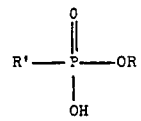

where R' is a substantially unbranched paraffinic alkyl group containing from about 10 to about 36 carbon atoms, and R is a hydrocarbyl group containing from 1 to about 4 carbon atoms with at least one hydrogen atom present on the carbon atom which is bonded to oxygen and (b) a substituted imidazoline of the formula:

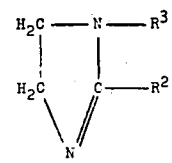

where one of the $R^2$ and $R^3$ substituents must be a substantially unbranched paraffinic or olefinic hydrocarbyl group containing from about 12 to about 35 carbon atoms; and the other $R^2$ or $R^3$ substituent is selected from the group consisting of: paraffinic alkyl containing from 1 to about 35 carbon atoms, alkenyl containing from 2 to about 35 carbon atoms, substituted alkyl containing from 1 to about 20 carbon atoms and substituted alkenyl containing from 2 to about 20 carbon atoms, wherein said substituents are selected from the group consisting of hydroxy, alkoxy, alkoxy-methoxy and oxo are provided. The alkylamine salts are contemplated for use as anti-wear agents and friction modifiers for lubricating oils and greases.

2 Claims, No Drawings

IMIDAZOLINE SALTS OF ACID PHOSPHONATES

CROSS-REFERENCE TO RELATED APPLICATIONS

This application is a continuation-in-part of application Ser. No. 840,924 filed Oct. 11, 1977, now abandoned which is a division of application, Ser. No. 733,581, filed Oct. 18, 1976, now U.S. Pat. No. 4,070,294, which is a continuation-in-part of application, Ser. No. 544,245, filed Jan.

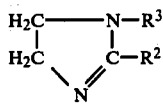

27, 1975, now abandoned, which is a continuation-in-part of application, Ser. No. 386,481, filed Aug. 7, 1973, and now abandoned.

BACKGROUND OF THE INVENTION

1. Field of the Invention

This invention relates to lubricant compositions and in one of its aspects relates more particularly to improved lubricant compositions, in the form of lubricating oils and greases, which normally require improvement in anti-wear and friction modifying properties.

2. Description of the Prior Art

It is well known that certain types of lubricant compositions, particularly oils of lubricating viscosities and greases normally exhibit poor anti-wear properties during the course of their performance, as well as requiring friction modifying improvement. In this respect, the prior art has heretofore attempted to employ various phosphonic acids, which has resulted in little or no improvement with respect to enhancement of anti-wear, anti-rust, storage stability and water tolerance properties of the lubricant, and in addition, requiring friction modifying improvement.

In British Pat. No. 1,247,541, salts of non-cyclic amines and alkyl alkane acid phosphonates are shown to be useful as friction modifiers. U.S. Pat. No. 3,793,199 discloses salts of alkyl alkane phosphonates and non-cyclic amines. Neither of these patents described the substituted imidazoline reactant of the present invention. Canadian Pat. No. 668,735 teaches n-amino alkyl substituted imidazoline salts of alkyl phosphonates as extreme pressure agents. Nowhere does this reference teach the salts of the alkyl and hydroxy alkyl substituted imidazolines and alkyl, long chain alkyl acid phosphonate of the present invention.

SUMMARY OF THE INVENTION

It has now been found that improvement in anti-wear and friction modifying properties of lubricant compositions, particularly lubricating oils and greases, can be realized by incorporating, in these compositions salts of (a) an alkyl alkane acid phosphonate having the formula:

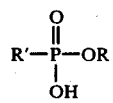

where R' is a substantially unbranched paraffinic alkyl group containing from about 10 to about 36 carbon atoms, but preferably is a substantially unbranched paraffin alkyl group containing from about 10 to about 20 carbon atoms, and most preferably is octadecyl; and R is a hydrocarbyl group containing from 1 to about 4 carbon atoms with at least one hydrogen atom present on the carbon atom which is bonded to oxygen, but R preferably is methyl or ethyl and most preferably is methyl; with (b) a substituted imidazoline of the formula:

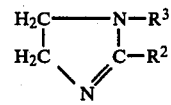

where one of the $R^2$ and $R^3$ substituents must be a substantially unbranched paraffinic or olefinic hydrocarbyl group containing from about 12 to about 35 carbon atoms; and the other $R^2$ or $R^3$ substituent is selected from the group consisting of: paraffinic alkyl containing from 1 to about 35 carbon atoms, alkenyl containing from 2 to about 35 carbon atoms and hydroxy, alkoxy-, alkoxymethoxy-, and oxo-substituted alkyl and alkenyl containing from 1 to about 20 carbon atoms.

It is preferred that $R^2$ be a substantially unbranched paraffin or olefin hydrocarbyl group containing from 12 to about 35 carbon atoms, and most preferred that $R^2$ be a substantially unbranched alkenyl group containing from about 13 to about 21 carbon atoms; with an alkenyl group containing 17 carbon atoms being the most particularly preferred group.

The preferred $R^3$ substituent is an alkyl group containing 1 to 20 carbon atoms, which most preferably is substituted with a hydroxy, alkoxy, alkoxymethoxy or oxo group. Of these, the particularly preferred substituent is a hydroxy substituted straight chain alkyl group containing from 2 to about 4 carbon atoms, with the —CH$_2$CH$_2$OH group being the most particularly preferred.

Non-limiting examples of the imidazoline compounds suitable for use herein include: 1-(2-hydroxycosanyl)-2-methylimidazoline, 1-(2-hydroxybutyl)-2-undecenylimidazoline, 1-(2-hydroxyhexyl)-2-tetradecylimidazoline, 1-(2-hydroxypropyl)-2-hexdecylimidazoline, 1-(2-hydroxyethyl)-2-heptadecenylimidazoline, 1-(2-hydroxyethyl)-2-octadecylimidazoline, 1-(2-hydroxyethyl)-2-dodecenylimidazoline, 1-(2-hydroxyoctadecyl)-2-heptadecylimidazoline, and 1-methyl-2-octadecenylimidazoline. The imidazoline compounds may be prepared by reaction of appropriately substituted 1,2-diaminoethanes with alkylcarboxylic acids as described in U.S. Pat. No. 2,267,965. A particularly preferred acid is oleic acid. Imidazolines which include examples of the above cited compounds are items of commerce as, for example, Amine C, Amine O and Amine S marketed by the Ciba-Geigy Corporation.

The alkylamine salt may be prepared, in general, by reacting, in stoichiometric proportions, a substituted imidazoline as described hereinabove and an alkyl, long chain alkyl acid phosphonate.

The reaction is carried out at ambient temperatures, although elevated temperatures may also be employed, where practical for hastening the reaction.

In general, the present invention in its preferred applications, contemplates organic lubricant compositions of the above-described types which contain a small amount of the aforementioned salts, preferably in an amount from about 0.2 to about 1.5%, by weight, and for most applications, in an amount from about 0.4 to about 1%, by weight, of the total weight of such compositions.

The organic lubricant compositions improved in accordance with the present invention may comprise any materials that normally exhibit insufficient anti-wear properties or which require friction modifying characteristics. A field of specific applicability is the improvement of liquid oils boiling within the range from about 75° F. to about 1000° F. Mineral lubricating oils, improved in accordance with the present invention may be of any suitable lubricating viscosity range from about 45 SSU at 100° F. to about 6000 SSU at 100° F. and, preferably, from about 50 to about 250 SSU at 210° F. These oils may have viscosity indexes varying from below 0 to about 100 or higher. Viscosity indexes from about 70 to about 95 are preferred. The average molecular weights of these oils may range from about 250 to about 800. In general, the lubricant may comprise any mineral or synthetic oil of lubricating viscosity.

As hereinbefore indicated, the aforementioned salts of the present invention may be incorporated as friction modifiers or anti-wear agents in grease compositions. Such greases may comprise a combination of a wide variety of lubricating vehicles and thickening or gelling agents. Thus, greases in which the aforementioned salts are particularly effective, may comprise any of the aforementioned oils of lubricating viscosity, as the oil vehicle, and may include mineral or synthetic lubricating oils, and, particularly of the types hereinbefore described. Then high temperature stability is not a requirement of the finished grease, mineral oils having a viscosity of at least 40 SSU at 150° F., and particularly those falling within the range from about 60 SSU to about 6000 SSU at 100° F. may be employed. The lubricating vehicles of the improved greases of the present invention containing the above-described salts, are combined with a grease-forming quantity of a thickening agent. For this purpose, a wide variety of materials may be employed. These thickening or gelling agents may include any of the conventional metal salts or soaps, which are dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolved when used at the required temperature within a particular environment; however, in all other respects any material which is normally employed for thickening or gelling hydrocarbon fluids for forming greases can be used in preparing the aforementioned improved greases in accordance with the present invention.

DESCRIPTION OF SPECIFIC EMBODIMENTS

The following data and examples will serve to illustrate the novel alkylamine salts of the present invention and their efficacy as lubricant improvers in anti-wear and friction modifying characteristics in organic lubricant compositions. It will be understood, however, that it is not intended the invention be limited to the particular additives as described and that various modifications thereof can be employed and will be readily apparent to those skilled in the art.

EXAMPLE 1

In the comparative runs of this example, the additive package component comprised, by weight: zinc dithiophosphate 1%, polymethyl methacrylate 3.3%, aromatic oil swelling agent 2%, kerosene 0.1%, calcium sulfonate 8.6%, synthetic sulfurized sperm oil 3%. In this example and in the remaining examples the base oil comprised a solvent-refined paraffin base oil stock dewaxed to a 0° F. pour point.

| | Run A | Run B |
|---|---|---|
| Formulation Material, Wt. % | | |
| Base Oil | 81.75 | 81.50 |
| Additive package | 18.00 | 18.00 |
| Methyl octadecyl acid phosphonate | 0.25 | 0.25 * |
| 1-(2-hydroxy ethyl)-2-heptadecenyl imidazoline | 0.00 | 0.25 * |
| Test Results | | |
| SAE Wear Test, 680607, 76 RMP, 150 lbs., ½hr. | | |
| Weight loss, mg | Fail in 10 Min. | 12 |
| Assessment | Fail | Pass |
| IHC Water Tolerance Test | | |
| 14 days with 1% water | | |
| Separation of additive, Vol. % | 0.2 | None |

*Reacted before blending

The comparative data of the foregoing example illustrates the improved anti-wear and water tolerance properties imparted by the salts of the present invention.

EXAMPLE 2

In the comparative runs of this example, the additive package component comprised, by weight, the same additive package employed in Example 1 except that the sulfurized sperm oil was omitted.

| | Run A | Run B |
|---|---|---|
| Formulation Material, Wt. % | | |
| Base Oil | 84.75 | 84.50 |
| Additive package | 15.00 | 15.00 |
| Methyl octadecyl acid phosphonate | 0.25 | 0.25 * |
| 1-(2-hydroxy ethyl)-2-heptadecenyl imidazoline | 0.00 | 0.25 * |
| Test Results | | |
| SAE Wear Test, 680607, 76 RPM 150 lbs., ½hr. | | |
| Weight loss, mg | 19 | 5 |
| Assessment | Pass | Pass |
| IHC Water Tolerance Test (1% Water) | | |
| Additive separation after 14 days, Vol. % | 0 | 0 |
| Additive separation after 21 days, Vol. % | 0.6 | 0 |
| Additive separation after 28 days, Vol. % | 0.8 | 0 |

*Reacted before blending

The comparative data of the foregoing example illustrates the improved anti-wear and water tolerance properties imparted by the salts of the present invention.

EXAMPLE 3

In the comparative runs of this example, the additive package component comprised, by weight: zinc dithiophosphate 0.7%, polymethyl methacrylate 3%, aromatic oil swelling agent 2%, kerosene 0.1%, calcium sulfonate 7%. The John Deere Tractor Chatter Index test is fully described in U.S. Pat. No. 3,652,410.

|  | Run A | Run B |
|---|---|---|
| Formulation Material, Wt. % |  |  |
| Base Oil | 86.70 | 86.70 |
| Additive package | 12.80 | 12.80 |
| Methyl octadecyl acid phosphonate | 0.50 | 0.25 * |
| 1-(2-hydroxy ethyl)-2-heptadecenyl imidazoline | 0.00 | 0.25 * |
| Test Results |  |  |
| John Deere Tractor Chatter Index | 184 | 186 |
| 4 Ball Wear Scar, mm (40 kg, 2 hrs., 200° (F., 600 rpm) | 0.50 | 0.45 |

*Reacted before blending

The comparative data of the foregoing example illustrates the improved anti-wear performance and equivalent chatter control imparted by the salts of the present invention.

EXAMPLE 4

In the comparative runs of this example, the additive package component comprised, by weight: polymethyl methacrylate 2.4%, sulfurized isobutylene 1.8%, polybutenyl succinimide of tetraethylpentamine 1%, kerosene 0.75%, alkyl ester of alkyl dithiophosphoric acid 0.2%, alkyl derivative of 2,5 dimercapto 1,3,4 thiadiazole 0.1%.

|  | Run A | Run B |
|---|---|---|
| Formulation Material, Wt. % |  |  |
| Base Oil | 93.25 | 93.25 |
| Additive package | 6.25 | 6.25 |
| Methyl octadecyl acid phosphonate | 0.50 | 0.25 * |
| 1-(2-hydroxy ethyl)-2-heptadecenyl imidazoline | 0.00 | 0.25 * |
| Test Results |  |  |
| Precipitate after 30 days storage at room temperature | Heavy | None |

*Reacted before blending

The comparative data of the foregoing example illustrates the inefficacy of the methyl octadecyl acid phosphonate, as a free acid, by forming a precipitate after 30 days.

EXAMPLE 5

In the comparative runs of this example, the additive package component comprised, by weight: polymethyl methacrylate 2.4%, sulfurized isobutylene 1.8%, polybutenyl succinimide of tetraethylpentamine 1.0%, alkyl ester of alkyl dithiophosphoric acid 0.2%, dibutylphosphonate 0.4% kerosene 0.75%, alkyl derivative of 2,5 dimercapto 1,3,4 thiadiazole 0.1%.

|  | Run A | Run B |
|---|---|---|
| Formulation Material, Wt. % |  |  |
| Base Oil | 93.35 | 92.85 |
| Additive package | 6.65 | 6.65 |
| Methyl octadecyl acid phosphonate | 0.00 | 0.25 * |
| 1-(2-hydroxy ethyl)-2-heptadecenyl imidazoline | 0.00 | 0.25 * |
| Test Results |  |  |
| John Deere Oxidation Test (100 hrs. at 300° F.) |  |  |
| % Viscosity change at 210° F. | 4.30 | 2.74 |
| % Viscosity change at 100° F. | 12.44 | 7.41 |
| Humidity Cabinet, 120° F. |  |  |
| Hours to rust | 24 | 48 |

*Reacted before blending

The comparative data of the foregoing example illustrates the improved performance in areas of oxidative stability and anti-rust properties imparted by the salts of the present invention.

EXAMPLE 6

In the comparative runs of this example, the additive package component comprised, by weight: polymethyl methacrylate 2.4%, polybutenyl succinimide of tetraethylpentamine 1.0%, barium sulfonate 1.0%, alkyl ester of aryl dithiophosphoric acid 2%, kerosene 0.1%.

|  | Run A | Run B |
|---|---|---|
| Formulation Material, Wt. % |  |  |
| Base Oil | 93.50 | 93.00 |
| Additive package | 6.50 | 6.50 |
| Methyl octadecyl acid phosphonate- | 0.00 | 0.25 * |
| 1-(2-hydroxy ethyl)-2-heptadecenyl imidazoline | 0.00 | 0.25 * |
| Test Results |  |  |
| Humidity Cabinet, 120° F. |  |  |
| Rating at 96 hours | Fail | Pass |
| SAE Wear Test |  |  |
| 76 RPM, 150 lbs. wt. loss, mg. Failed at 150 lbs. | 74 |  |
| 156 RPM, 400 lbs. wt. loss, mg. Failed at 180 lbs. | 877 |  |

*Reacted before blending

The comparative data of the foregoing example illustrates the improvement in anti-wear and anti-rust performance imparted by the salts of the present invention.

The examples of the following Table I demonstrates the results obtained when the base oil, in which no additive other than the reactants and the salt of the present invention is employed, is subjected to oxidation, wear and friction testing. The base oil in each of the examples comprised a solvent-refined paraffin base oil stock dewaxed to 0° F. pour point.

TABLE I

|  | Example 1 | Example 2 | Example 3 | Example 4 |
|---|---|---|---|---|
| Base oil | 100 wt % | 99.75 wt % | 99.75 wt % | 99.5 wt % |
| acid phosphonate | 0.00 wt % | 0.25 wt % | 0.00 wt % | 0.25 wt % * |
| 1-(2-hydroxy ethyl)-2-heptadecenyl imidazoline | 0.00 wt % | 0.00 wt % | 0.25 wt % | 0.25 wt % * |
| Oxidation (80 hrs 260° F.) (10 l air/hr) |  |  |  |  |

TABLE I-continued

|  | Example 1 | Example 2 | Example 3 | Example 4 |
|---|---|---|---|---|
| (Pb, Cu, Al, Fe Catalysts) | | | | |
| % Change in Viscosity at 210° F. | 11 | 450 | 237 | 183 |
| 4 Ball Wear Scar, mm (40 kg, 1 hr, 200° F., 600 RPM) | 0.625 | 0.400 | 0.700 | 0.400 |
| Friction (LVFA) | | | | |
| Static at 100° F. | 0.170 | 0.097 | 0.100 | 0.085 |
| 200° F. | 0.238 | 0.060 | 0.090 | 0.050 |
| 275° F. | 0.245 | 0.046 | 0.060 | 0.036 |

*Reacted before blending

From Table I, it will be noted that the base oil exhibits relatively good oxidation stability, but has poor anti-wear properties and high static friction. Individually, the phosphonate and the substituted imidazoline give reduced oxidation stability, and both lower the static friction, but the phosphonate improves the anti-wear properties and the imidazoline affects it adversely. The combination of the base oil, phosphonate and imidazoline improve the oxidation stability over that of either the imidazoline or phosphate alone, the good anti-wear properties of the phosphonate are retained and the static friction is reduced below that of the imidazoline or phosphonate alone.

While preferred embodiments of the novel organic lubricant compositions of the present invention have been described for the purpose of illustration, it will be understood that various modifications and adaptations, thereof, which will be obvious to those skilled in the art, may be made without departing from the spirit of the invention.

What is claimed is:

1. A salt of methyl octadecyl acid phosphonate and 1-(2-hydroxy ethyl)-2-heptadecenyl imidazoline.

2. The salt of claim 1 wherein said imidazoline and said phosphonate are present in stoichiometric proportions.

* * * * *

UNITED STATES PATENT AND TRADEMARK OFFICE
CERTIFICATE OF CORRECTION

PATENT NO. : 4216334
DATED : August 5, 1980
INVENTOR(S) : DANIEL G. JONES

It is certified that error appears in the above-identified patent and that said Letters Patent are hereby corrected as shown below:

Column 1, between lines 12 to 18, this formula should be deleted entirely.

Column 3, line 53, "dissolved" should be --dissolve--.

Column 5, line 20, before "F" delete "(".

Column 6, line 19, insert --*-- before "Reacted".

Column 6, table I, under "Base Oil" and above "acid phosphonate" insert --Methyl octadecyl--.

Signed and Sealed this

Ninth Day of December 1980

[SEAL]

Attest:

SIDNEY A. DIAMOND

Attesting Officer

Commissioner of Patents and Trademarks